(12) United States Patent
Lowe et al.

(10) Patent No.: US 7,978,333 B2
(45) Date of Patent: Jul. 12, 2011

(54) HOLOGRAPHIC SENSOR HAVING HETEROGENEOUS PROPERTIES

(75) Inventors: Christopher Robin Lowe, Cambridge (GB); Anthony Peter James, Warwickshire (GB); Edward Rayne, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 750 days.

(21) Appl. No.: 11/572,244

(22) PCT Filed: Jul. 19, 2005

(86) PCT No.: PCT/GB2005/002846
§ 371 (c)(1),
(2), (4) Date: Jul. 8, 2007

(87) PCT Pub. No.: WO2006/008524
PCT Pub. Date: Jan. 26, 2006

(65) Prior Publication Data
US 2007/0285667 A1    Dec. 13, 2007

(30) Foreign Application Priority Data
Jul. 19, 2004    (GB) .................................. 0416132.9

(51) Int. Cl.
*G01B 9/021*    (2006.01)
(52) U.S. Cl. ...................................................... 356/457
(58) Field of Classification Search .................. 356/457, 356/458
See application file for complete search history.

(56) References Cited

U.S. PATENT DOCUMENTS

| | | | |
|---|---|---|---|
| 5,857,709 A | 1/1999 | Chock et al. | |
| 5,874,187 A * | 2/1999 | Colvin et al. | 430/2 |
| 6,087,940 A * | 7/2000 | Caperna et al. | 340/572.5 |
| 6,160,645 A * | 12/2000 | Chandross et al. | 359/3 |
| 6,165,648 A * | 12/2000 | Colvin et al. | 430/1 |
| 6,322,931 B1 * | 11/2001 | Cumpston et al. | 430/1 |
| 6,512,606 B1 * | 1/2003 | Lipson et al. | 359/3 |
| 6,627,354 B1 * | 9/2003 | Chandross et al. | 430/1 |
| 6,987,592 B2 * | 1/2006 | Tsukagoshi | 359/35 |
| 7,129,006 B2 * | 10/2006 | Hesselink et al. | 430/1 |
| 2001/0030934 A1 * | 10/2001 | Lipson et al. | 369/275.4 |
| 2004/0009406 A1 * | 1/2004 | Hesselink et al. | 430/1 |
| 2007/0285667 A1 * | 12/2007 | Lowe et al. | 356/457 |

FOREIGN PATENT DOCUMENTS

| | | |
|---|---|---|
| EP | 0345405 | 12/1989 |
| JP | 02-256086 | 10/1990 |
| JP | 07-084503 | 3/1995 |

(Continued)

OTHER PUBLICATIONS

Chen, G. et al., "A New Temperature- and pH-Responsive Copolymer for Possible Use in Protein Conjugation," *Macromolecular Chemistry and Physics*, 1995, p. 1251-1259, vol. 196, Wiley-VCH, Weinheim, DE.

Ley, C., et al., "Holographic Gratings Recorded in Polymer Hydrogels—An Original Application as a Sensor in Aqueous Environment," Sep. 1997, p. 997-1000, vol. 8, No. 9, Measurement Science & Technology IOP Publishing, UK.

(Continued)

*Primary Examiner* — Patrick J Connolly
(74) *Attorney, Agent, or Firm* — Saliwanchik, Lloyd & Eisenschenk

(57) ABSTRACT

A sensor which comprises a support medium and a hologram disposed therein, wherein an optical characteristic of the medium varies as a result of a change of a property of the medium, and wherein the medium is heterogeneous such that the change of property is heterogeneous.

43 Claims, 4 Drawing Sheets

FOREIGN PATENT DOCUMENTS

| | | |
|---|---|---|
| JP | 10-126002 | 5/1998 |
| JP | 2004-114546 | 4/2004 |
| WO | WO 95/26499 | 10/1995 |
| WO | WO 99/63408 | 12/1999 |
| WO | WO 01/50113 | 7/2001 |
| WO | WO 01/71322 | 9/2001 |
| WO | WO 03/087899 | 10/2003 |
| WO | WO 2004/081546 | 9/2004 |
| WO | WO 2004/081676 | 9/2004 |

OTHER PUBLICATIONS

Marshall, A. et al., "pH-Sensitive Holographic Sensors," *Analytical Chemistry*, Sep. 1, 2003, p. 4423-4431, vol. 75, No. 17, American Chemical Society, Columbus, US.

Mayes, A. et al., "A Holographic Sensor Based on a Rationally Designed Synthetic Polymer," *Journal of Molecular Recognition*, 1998, p. 168-174, vol. 11, No. 1-6, Heyden & Son LTD, London, GB.

* cited by examiner

HOLOGRAPHIC SENSOR HAVING HETEROGENEOUS PROPERTIES

CROSS-REFERENCE TO A RELATED APPLICATION

This application is a National Stage Application of International Application Number PCT/GB2005/002846, filed Jul. 19, 2005; which claims priority to Great Britain Application No. 0416132.9, filed Jul. 19, 2004.

FIELD OF THE INVENTION

This invention relates to a holographic sensor, and to its production.

BACKGROUND TO THE INVENTION

Holographic sensors may be used for the detection of a variety of analytes. WO95/26499 discloses a holographic sensor, based on a volume hologram. This sensor comprises an analyte-sensitive matrix having an optical transducing structure disposed throughout its volume. Because of this physical arrangement of the transducer, the optical signal generated by the sensor is very sensitive to volume changes or structural rearrangements taking place in the analyte-sensitive matrix as a result of interaction or reaction with the analyte.

SUMMARY OF THE INVENTION

According to a first aspect of the invention, a sensor comprises a support medium and a hologram disposed therein, wherein an optical characteristic of the medium varies as a result of a change of a property of the medium, and wherein the medium is heterogeneous such that the change of property is heterogeneous.

According to another aspect of the invention, a method for the production of a holographic sensor comprises the steps of:
  forming a heterogeneous support medium by:
    (a) polymerisation of monomers, wherein at least one of the polymerisation reaction conditions is varied during polymerisation; or
    (b) introducing into a medium a component, reacting the component with the medium or a second component present in the medium, and varying the extent of reaction occurring in the medium;
  disposing in the support medium a holographic recording material; and
  recording a holographic image.

This method allows the sensitivity of the sensor to be accurately predetermined. An array of sensors produced by a method of the invention may comprise sensors having different, scaled sensitivities.

Another aspect of the invention is a method for the production of a sensor which comprises a medium and a hologram disposed therein, wherein an optical characteristic of the medium varies as a result of a change of a property of the medium, the method comprising the steps of:
  forming a support medium by polymerising a mixture of polymerisable components and another component;
  disposing in the support medium a holographic recording material; and
  recording a holographic image;
wherein the temperature at which the change of the physical property occurs is dependent on the amount of the another component present in the mixture. The optical characteristic may vary as a result of the medium undergoing a phase transition.

According to a further aspect of the invention, a method for the production of a silver-free holographic sensor comprises the steps of:
  forming a heterogeneous support medium having a hologram disposed throughout the volume of the medium by:
    (1) introducing throughout the volume of a first polymer a cross-linking monomer mixture;
    (2) reacting the monomer mixture to create a second polymer having a holographic image recorded therein, where the first and second polymer form the medium and wherein the extent of reaction is varied throughout the medium.

The invention provides sensors which may be particularly useful in the field of security. For example, the sensitivity of a sensor of the invention may be so varied and complex that making an exact copy of the sensor is virtually impossible.

DESCRIPTION OF THE INVENTION

Figure 1:
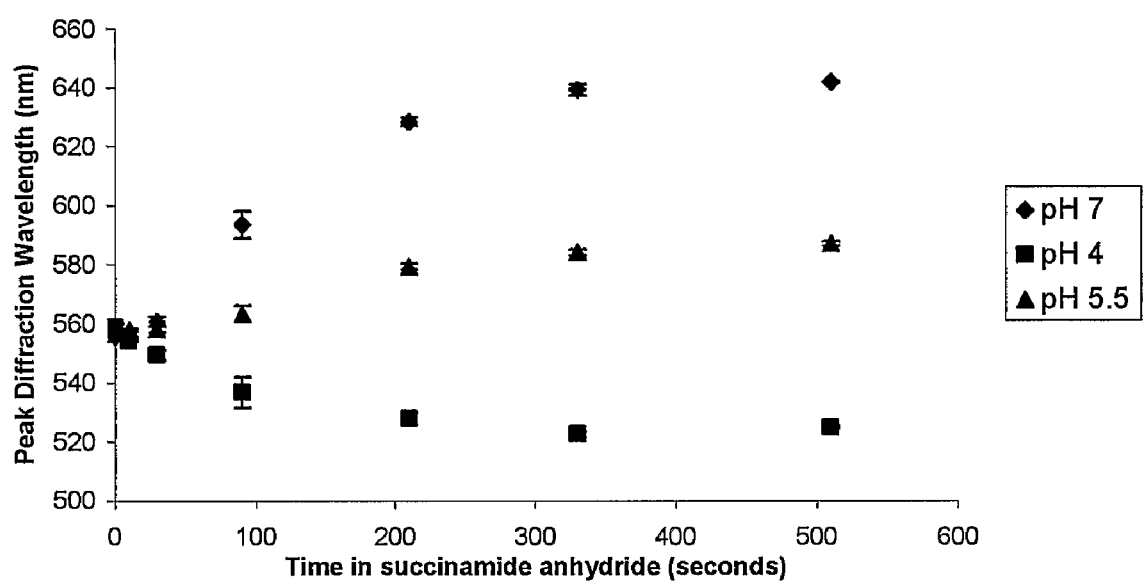
FIG. 1 is a graph of peak diffraction wavelength (nm) against time (sec) in succinic anhydride at different pH values.

The heterogeneity exhibited by a sensor of the invention may be random. Alternatively, the sensor may comprise a substantially continuous or gradual/stepwise change of properties. This may allow the senor to have a scale of responses associated with it, e.g. a plurality of zones of different properties/reactivities.

A sensor of the invention preferably comprises a polymeric support medium. Heterogeneity may be achieved by varying the degree of polymerisation through the medium, i.e. so that the medium comprises a substantially polymerised region and a relatively less polymerised region. In this case, the regions may be such that, at a particular analyte concentration or range of concentrations, the value of the optical characteristic is the same or substantially the same in each region.

Preferably, the polymeric medium comprises functional groups that can be readily modified. For example, it may be formed from hydroxyethyl methacrylate ("HEMA"), aminoethyl methacrylate ("AEMA") and/or ethylene diglycol methacrylate ("EDMA") monomers. A resultant polymer comprises an amino functional group which may be readily modified. Amino groups may be modified, for example, using an anhydride such as acetic anhydride, succinic anhydride or 4-nitrophthalic anhydride.

The use of different polymerisable components allows different sensitivities to be obtained, for example, in a single holographic element. Below pH 4, a holographic element comprising HEMA/AEMA modified with succinic anhydride replays at approximately the same wavelength as HEMA/AEMA modified with acetic anhydride. Thus, an element having a HEMA/AEMA polymeric medium comprising succinic anhydride-modified and acetic anhydride-modified regions can be used as a pH sensor; when the colour of each region appears to be the same, the user would know that the pH is less than 4. A similar effect is observed when comparing acetic anhydride-modified and unmodified HEMA/AEMA for pH >8.5.

A hologram may be disposed throughout the volume of the support medium. A sensor of the invention may comprise a holographic element having a "sensitivity gradient". The gradient may be obtained by varying the extent to which the polymeric medium is modified, i.e. the degree of polymerisation is graded. This may be achieved by differential exposure of the medium to (de)polymerisation conditions.

A holographic element having a substantially modified medium may have a greater span of replay wavelength for a given range of analyte concentration compared with a less modified one. In this case, if a substantially modified region and a relatively less modified region both replay at the same wavelength, then this may indicate that each region is subject to a different analyte concentration. Therefore, at a particular point along a sensitivity gradient, a given colour will be indicative of a particular analyte concentration. At a different point along the gradient, the same colour will be indicative of a different analyte concentration. Thus, if a sensor comprises a holographic element comprising a sensitivity gradient, a standard reference colour can be employed to calibrate the gradient in terms of analyte concentration.

A method of the invention may comprise introducing an additional monomer to the polymer followed by further polymerisation. For example, the additional monomer may be obtained by deprotecting a protected monomer already present in the polymerisation mixture. Monomers may be protected with groups such as N-(t-butoxycarbonyl), prior to the initial polymerisation. The polymerised mixture will then comprise polymerised and non-polymerised regions. The protected monomers can then be selectively deprotected and polymerised. This allows accurate scaling of the sensitivity of the sensor.

Alternatively, the additional component may be a cross-linker, the polymer comprising cross-linkable groups which can be selectively cross-linked. Cross-linking is another means of precisely controlling the polymer structure and thus the sensitivity of the holographic element. Particularly preferred is photochemical cross-linking involving the use of a variable (e.g. grey-scale) mask, to achieve the desired varied response.

The sensitivity of the holographic element can be controlled using an agent such as a chromate. The use of a chromate with gelatine-based support media (in particular those cross-linked with formaldehyde), may reduce the sensitivity of the element, while at the same time increasing its replay wavelength.

In this embodiment, a first step is to create a gelatine polymer, which is not cross-linked on a substrate. A gelatine solution in water is coated onto a suitable substrate, e.g. glass or a plastic which has been treated to allow gelatine adhesion. The gelatine is allowed to cool and set.

Once set, the gelatine can be treated with different concentrations of, say, chromium ions, causing a differential cross-linking and therefore a differential sensitivity. This can be achieved in a number of ways. One example is to create a bath into which the whole gelatine film can be lowered. The bath contains a cold chromium solution, with 1-5% or more chromium ions. The whole film is lowered into the bath and then immersed in the chromium solution. The film is then raised out of the chromium solution slowly so that the sections which have been soaked in the solution longer have a greater cross linking density.

A similar effect may be achieved by flowing 2 solutions into the bath containing the gelatine film. One is a concentrated chromium solution and the other water. The concentration of chromium will decrease over time if the rate of water addition is higher than that of the chromium solution. The gradient can be reversed by increasing the rate of chromium solution addition rather than water addition.

This principle is equally adaptable to the use of glutaraldehyde solutions as the cross-linker rather than a chromium solution. The cross-linked polymer can then be turned into a hologram, e.g. by diffusion, as described in, for example, WO95/26949.

A holographic sensor may be designed to have an enhanced response upon reaction with an analyte. In such a sensor, the holographic element preferably comprises a hydrogel-based support medium which, upon reaction with an analyte, undergoes a phase transition, for example towards a glassy state. Associated with this phase transition is a shift in an optical characteristic, such as the peak wavelength of diffraction; the magnitude of the shift is dependent on the temperature. At a particular (generally elevated) temperature, a maximum shift is observed. It has been discovered that, by adding copolymers to the initial polymer and further polymerising, the temperature at which this "super-response" occurs can be varied. Therefore a sensor to be used at a specific temperature can be designed so that its maximum response occurs at that temperature.

Most holographic sensors rely on silver to form a hologram. However, it can be advantageous to produce silver-free holographic sensors. Silver-free sensors can be made with a heterogeneous medium to produce sensors with a scaled sensitivity as follows. A sensor polymer is produced (P1) and a second polymerisation is carried out using a cross-linking monomer mixture (P2) to produce hard, cross-linked polymer fringes and thereby create a hologram within P1. Polymerisation of P2 is carried out by exposure of the P2 mixture, which has been soaked into P1, to a UV laser.

The time of exposure of the P2 mixture to the UV laser will affect the extent of the cross-linking and hardness of the P2 polymer. This in turn affects the sensitivity of the resulting holographic sensor. As such, a virtual instrument could be manufactured using this technique whereby differing sensitivities are achieved by exposing the sensor with the P2 mixture to the UV laser for different amounts of time.

A silver-free technique of the type described in WO2004/081676 can be used to create single holograms with two distinct sensitivities. The concept is based on the use of one sensitivity in the initial polymer (P1) and a second sensitivity in the fringes of the polymer (P2).

More particularly, by comparison with WO2004/081676, a second sensitivity is added by creating a P2 mixture which contains ligands for a second analyte. The net effect of swelling or contraction of the P2 fringes will result in an alteration of the refractive index difference between P2 and P1, thereby resulting in a change in brightness. By contrast, binding of analyte to P1 results in swelling of the overall polymer and a change in the wavelength of the signal with minimal change in the refractive index. Thus, the 2 signals can be separated on the basis of wavelength shift versus intensity shift.

The sensor of the present invention can comprise a hologram generated by the diffraction of light. The hologram may only be visible under magnification, white light, UV light or infra-red radiation or may be viewed under specific temperature, magnetism or pressure conditions. The holographic image may be of an object or have a 2- or 3-dimensional effect. The sensor may comprise means for producing an interference effect when illuminated with laser light, where the means may comprise a depolarising layer.

The sensor may be sensitive to an analyte which is a chemical, biochemical or biological species. The present invention relates to a method of detection of any such analyte in a sample, which comprises contacting the sample with the sensor, and detecting any change of its optical characteristic.

The present invention also relates to an article comprising a sensor according to the invention where the article is a device such as a transaction card, banknote, passport, identification card, smart card, driving licence, share certificate, bond, cheque, cheque card, tax banderole, gift voucher, postage stamp, rail or air ticket, telephone card, lottery card, event ticket, credit or debit card, business card, or an item used in consumer, brand or product protection for the purpose of distinguishing genuine products from counterfeit products or identifying stolen products. The article can also be an item of intelligent packaging which is a system that comprises a container, wrapper or enclosure to monitor, test or indicate product information on quality or environmental conditions that will affect product quality, shelf life or safety. Typical applications include indicators showing time-temperature, freshness, moisture, alcohol, gas, physical damage and the like.

The article can be an industrial or handicraft item comprising a decorative element, selected from items of jewellery, items of clothing (including footwear), fabric, furniture, toys, gifts, household items (including crockery and glassware), architecture (including glass, tile, paint, metals, bricks, ceramics, wood, plastics and other internal and external installations), art (including pictures, sculpture, pottery and light installations), stationery (including greetings cards, letterheads and promotional material) and sporting goods. The article can be a product or device for use in agricultural studies, environmental studies, human or veterinary prognostics, theranostics, diagnostics, therapy or chemical analysis which can be a test strip, chip, cartridge, swab, tube, pipette, contact lens, sub-conjunctival implant, sub-dermal implant, breathalyser, catheter or a fluid sampling or analysis device.

The invention also relates to a transferable holographic film comprising a sensor according to the invention. The film can be present on a hot stamping tape or can be used to enhance the security of an article, by transferring onto the article the sensor from the film.

The present invention further relates to a product comprising a sensor of the invention which is capable of generating data and a system which uses such data for data reading, processing, storage, control, transmission, distributing, reporting and/or modelling. Such systems include mobile telephones, personal digital assistants and other portable electronic devices.

The following Examples illustrate the invention. Examples 1 to 3 are of sensors containing silver; Examples 4 and 5 are silver-free. DMPA is 2,2-dimethoxy-2-phenylacetophenone. HYPO is 20% (w/v) sodium thiosulphate in water. QBS is 1,1'-diethyl-2,2'-cyanine iodide.

Preparation of Slides for Sensors in Examples 1 to 3

A polymer was prepared using 0.3 mmol of monomers per slide. The slides were presubbed using 3-(trimethoxysilyl) propyl methacrylate. The polymer solution (per slide) contained HEMA (34 mg), AEMA.HCl (4.95 mg), EDMA (1.52 mg), n-propanol (24.4 µl), and 5% DMPA in MeOH (2.71 µl). The solution was polymerised on the slides under UV light at 25° C. for 50 minutes. After polymerisation, each slide was washed with deionised water and ethanol.

Each slide was then treated with 0.3 M $AgClO_4$ in 80% n-propanol (200 µl) for 2 minutes and 15 seconds. The slides were allowed to dry and then agitated in 40 ml of 3% (w/v) LiBr in 70% methanol with 1 ml 0.1% (w/v) QBS in methanol for 2 minutes. Each slide was equilibrated in 1.0 M $Na_2SO_4$ with 2% (w/v) ascorbic acid (70 ml) for 10 minutes before exposure to a single pulse of a frequency doubled Nd:YAG pulse laser (532 nm).

The slides were developed in 2.5% (w/v) hydroquinone and 0.75% (w/v) NaOH in 50% methanol for one minute, followed by agitation in 5% (v/v) acetic acid to stop development. The slides were treated with HYPO (40 ml) which had been used previously for 2 minutes and then fresh HYPO for a further 2 minutes.

EXAMPLE 1

A slide was divided into sections and treated with succinic anhydride according to the following protocol: 2.5 g of succinic anhydride was added to a stirred solution of 0.1 M $NaH_2PO_4$ buffer (500 ml, pH 7.0) in a glass beaker. The slide with the hologram was inserted immediately into the solution, before the succinic anhydride had completely dissolved. The slide was lowered incrementally into the reaction solution at set time periods. Once this had been completed, the slides was washed thoroughly in deionised water immediately after removal, to remove any reactants and then washed in 100 mM NaOH followed by 5 mM $HNO_3$.

Slide sections were treated for 0, 10, 30 90, 210, 330 and 510 seconds using this method. The response of these treated slides at pH 4, pH 5.5 and pH 7 was then tested.

FIG. 1 shows the peak diffraction wavelength against time of treatment with succinic anhydride for the three different pH values. The results show that, the longer the medium is treated, the greater the range of wavelengths attained for a given pH range.

EXAMPLE 2

A section of a slide was treated in a cuvette with acetic anhydride (20 µl) in 0.1 M $NaH_2PO_4$ buffer (500 µl, pH 7.0). The reaction was monitored using a spectrometer and allowed to go to completion. Another section of the same slide was then reacted with succinic anhydride (0.0517 g) in $NaH_2PO_4$ buffer (500 µl, pH 7.0) for ten minutes. The slide was then tested in a variety of buffers with an ionic strength 500 mM.

Figure 2:
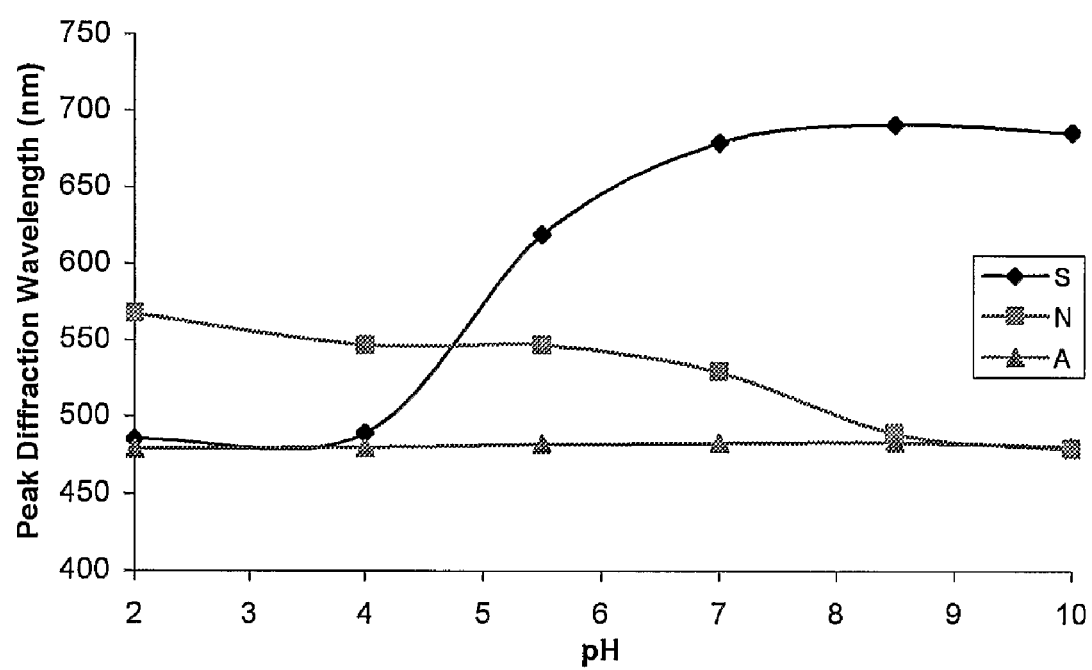
FIG. 2 is a graph of peak diffraction wavelength (nm) against pH for succinic anhydride (S), normal/untreated (N) or acetic anhydride (A)

The sensitivities of the unmodified, succinic anhydride-modified and acetic anhydride-modified portions are shown in FIG. 2. The succinic anhydride portion behaved in the opposite way to the untreated portion as the ring-opening of the anhydride generates a free acid group. The range of wavelengths of the succinic anhydride portion was much greater than that of the other two portions, spanning the entire visible region of the spectrum. At pH <4, the succinic and acetic anhydride portions replayed at about the same wavelength; a similar effect was observed for the unmodified and succinic anhydride-modified portions at pH >8.5.

EXAMPLE 3

A section of a slide was treated with acetic anhydride (1 ml) in $NaH_2PO_4$ buffer (250 ml, pH 7.0) while being stirred over ice, prior to recording a hologram in the polymer. Before the addition of silver, the slide was washed in 100 mM NaOH and 5 mM $HNO_3$. The slide was then exposed in $Na_2SO_4$ as described previously. Another section of the slide was treated with acetic anhydride (1 ml) in $NaH_2PO_4$ buffer (250 ml, pH 7.0) while being stirred over ice after a hologram had been recorded within the polymer.

A succinic anhydride gradient was formed in another section of the slide after hologram recording according to the protocol given in Example 1. The different sections of the slide were treated for 360, 240, 150, 120, 90 and 60 seconds respectively.

Figure 3:
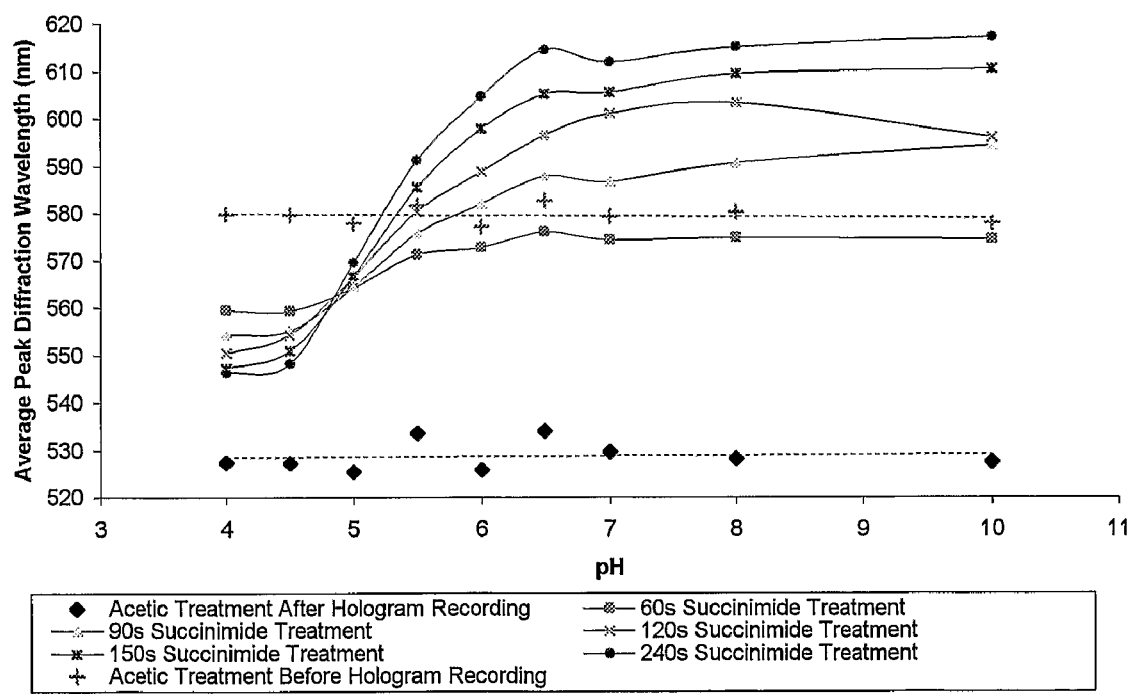
FIG. 3 is a graph of peak diffraction wavelength (nm) against pH under different conditions.

FIG. 3 shows the pH response of the succinic anhydride-modified portions and the acetic acid-modified portions. The peak diffraction wavelengths of the acetic acid-modified portions remained approximately constant over the selected pH range. The succinic anhydride portions, however, were highly sensitive to changes in pH, the sensitivity increasing with the period of treatment with the anhydride; this is shown by the large difference in wavelength between pH 4 and pH 10 for a 240 s treatment, relative to shorter treatment times.

EXAMPLE 4

A silver-free pH-sensitive holographic sensor was produced using a sensor polymer P1 and a cross-linking monomer mixture P2. P1 consisted of a polyHEMA (85 mol %) co-polymer with 10 mol % methacrylic acid (MAA) and 5 mol % ethylene glycol dimethacrylate (EDMA). The P2 mixture consisted of 20 mg Irgacure 2959, 7 ml methanol, 2 ml EDMA, 200 ml hydroxyethyl methacrylate (HEMA), 20 ml ethylene glycol and 20 ml water. Two separate sections of the P1 (on the same glass slide) were exposed for 15 and 30 seconds to a UV laser respectively to create silver-free holograms with P2 layers of differing hardness.

Figure 4:
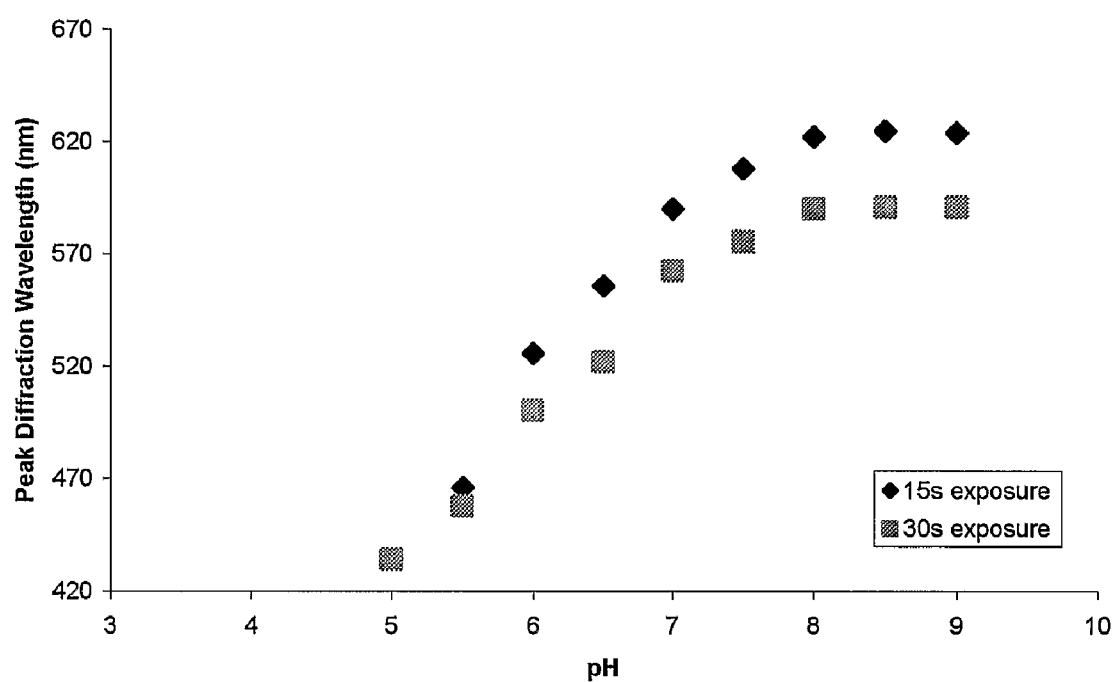
FIG. 4 is another graph of peak diffraction wavelength (nm) against pH under different conditions.

As seen in FIG. 4, the response of the resultant sensor system to pH (25 mM ionic strength, 30° C.) after 30 seconds of exposure to the UV laser was lower than that of the same system which only had 15 seconds of exposure. This demonstrates that the sensitivity of the holographic sensor can be tuned simply by controlling the amount of UV exposure. This system can be used on the same slide containing P1 resulting in a series of sensors, on a single substrate with tuned sensitivities for a particular application or a single sensor with a "graded" response.

EXAMPLE 5

A silver-free holographic sensor having two distinct sensitivities was created. The base polymer (P1) consisted of 64 mol % acrylamide, 32 mol % methacrylamide and 3 mol % methylenebisacrylamide polymerised in water. These polymers are sensitive to solvents such as ethanol as they are very hydrophilic and will contract in the presence of solvent. The P2 formula was made up from 100 ml 2% (w/v) ascorbic acid in water, 1 ml methanol, 4 ml water, 500 ml diethylene glycol, 5 mg Irgacure 2959, 5 mg DMPA, 0.4 g 1,4-bisacryloylpiperazine and 0.148 g acrylic acid. This creates a pH-sensitive P2 mixture and thus pH-sensitive fringes.

On testing the polymer, a hologram could be observed in pH 3 buffer (50 mM ionic strength). This would not affect the base P1 polymer. At pH 9 (50 mM ionic strength), the hologram disappeared. This is because the acidic groups in P2 had swelled in response to the pH 9 buffer, decreasing the difference in refractive index between P1 and P2 and causing the hologram to vanish.

The invention claimed is:

1. A sensor which comprises a support medium and a hologram disposed therein, wherein an optical characteristic of the sensor varies as a result of a change of a property of the medium, and wherein the medium is heterogeneous, comprising a plurality of zones of different properties/reactivities, such that the change of property is heterogeneous.

2. The sensor according to claim 1, wherein the medium is a polymer.

3. The sensor according to claim 2, wherein the medium comprises relatively more and less polymerised regions.

4. The sensor according to claim 3, for the detection of an analyte wherein, at a particular analyte concentration, the value of the optical characteristic is substantially the same in each region.

5. The sensor according to claim 1, wherein the optical characteristic is the diffraction, reflectance, refractance or absorbance of the holographic element.

6. The sensor according to claim 1, wherein the hologram is generated by the diffraction of light.

7. The sensor according to claim 1, wherein the hologram is only visible under magnification.

8. The sensor according to claim 1, wherein the holographic image is of an object or is a 2- or 3-dimensional effect.

9. The sensor according to claim 1, further comprising means for producing an interference effect when illuminated with laser light.

10. The sensor according to claim 1, wherein the hologram is viewable under white light, UV light or infra-red radiation.

11. The sensor according to claim 1, wherein the hologram is viewable under specific temperature, magnetism or pressure conditions.

12. The sensor according to claim 1, for the detection of a chemical, biochemical or biological species.

13. A method of detection of an analyte in a sample, which comprises contacting the sample with a sensor which comprises a support medium and a hologram disposed therein, wherein an optical characteristic of the sensor varies as a result of a change of a property of the medium, and wherein, prior to contact with the analyte, the medium is heterogeneous, comprising a plurality of zones of different properties/reactivities, such that the change of property is heterogeneous, and wherein said method further comprises detecting any change of its optical characteristics.

14. An article comprising a sensor which comprises a support medium and a hologram disposed therein, wherein an optical characteristic of the sensor varies as a result of a change of a property of the medium, and wherein the medium is heterogeneous, comprising a plurality of zones of different properties/reactivities, such that the change of property is heterogeneous.

15. The article according to claim 14, which is a transaction card; banknote; passport; identification card; smart card; driving licence; share certificate; bond; cheque; cheque card; tax banderole; gift voucher; postage stamp; rail or air ticket; telephone card; lottery card; event ticket; credit or debit card; business card; or an item used in consumer, brand or product protection for the purpose of distinguishing genuine products from counterfeit products or identifying stolen products.

16. The article according to claim 14, which is an item of intelligent packaging.

17. The article according to claim 14, which is an industrial or handicraft item comprising a decorative element, selected from items of jewellery, items of clothing, fabric, furniture, toys, gifts, household items, architecture, art, stationery and sporting goods.

18. The article according to claim 14, which is a product or device for use in agricultural studies, environmental studies, human or veterinary prognostics, theranostics, diagnostics, therapy or chemical analysis.

19. The article according to claim 18, which is a test strip, chip, cartridge, swab, tube, pipette, contact lens, sub-conjunctival implant, sub-dermal implant, breathalyser, catheter or a fluid sampling or analysis device.

20. A transferable film comprising a sensor which comprises a support medium and a hologram disposed therein, wherein an optical characteristic of the sensor varies as a result of a change of a property of the medium, and wherein the medium is heterogeneous, comprising a plurality of zones of different properties/reactivities, such that the change of property is heterogeneous.

21. The film according to claim 20, which is present on a hot stamping tape.

22. A method of enhancing the security of an article, which comprises transferring onto the article a transferable film comprising a sensor which comprises a support medium and a hologram disposed therein, wherein an optical characteristic of the sensor varies as a result of a change of a property of the medium, and wherein the medium is heterogeneous, comprising a plurality of zones of different properties/reactivities, such that the change of property is heterogeneous.

23. An apparatus comprising a sensor which comprises a support medium and a hologram disposed therein, wherein an optical characteristic of the sensor varies as a result of a change of a property of the medium, and wherein the medium is heterogeneous, comprising a hp of zones of different properties/reactivities, such that the change of property is heterogeneous, and wherein said apparatus further comprises a means for generating and/or recording data from the sensor.

24. A system which uses, for data storage, control, transmission, reporting and/or modeling, data generated by an apparatus comprising a sensor which comprises a support medium and a hologram disposed therein, wherein an optical characteristic of the sensor varies as a result of a change of a property of the medium, and wherein the medium is heterogeneous, comprising a plurality of zones of different properties/reactivities, such that the change of property is heterogeneous, wherein said apparatus further comprises means for generating and/or recording data from the sensor.

25. A method for the production of a holographic sensor, which comprises the steps of:
   forming a heterogeneous support medium by the polymerisation of monomers, wherein at least one of the polymerisation reaction conditions is varied during polymerisation;
   disposing in the support medium a holographic recording material; and recording a holographic image.

26. A method for the production of a holographic sensor, which comprises the steps of:
   forming a heterogeneous support medium by introducing into a medium a component, reacting the component with the medium or a second component present in the medium, and varying the extent of reaction occurring in the medium;
   disposing in the support medium a holographic recording material; and recording a holographic image.

27. The method according to claim 26, wherein the medium is a polymer.

28. The method according to claim 26, wherein the medium comprises an amino group and the component is an anhydride.

29. The method according to claim 28, wherein the medium is obtainable by the polymerisation of monomers including hydroxyethyl methacrylate, aminoethyl methacrylate and/or ethyl dimethacrylate.

30. The method according to claim 28, wherein the component is succinic anhydride or acetic anhydride.

31. The method according to claim 26, wherein the medium is cross-linkable and the component is a cross-linker.

32. The method according to claim 26, wherein the component is polymerisable, the medium comprising a second component which is polymerisable.

33. The method according to claim 32, wherein the medium comprises protected monomers, the components being monomers obtainable by deprotection of protected monomers.

34. The method according to claim 25, wherein the image is recorded by contact-printing.

35. An array of discrete sensors, obtainable by a method for the production of a holographic sensor, which comprises the steps of:
   forming a heterogeneous support medium by the polymerisation of monomers, wherein at least one of the polymerisation reaction conditions is varied during polymerisation;
   disposing in the support medium a holographic recording material; and recording a holographic image.

36. The array according to claim 35, wherein the sensors have different sensitivities.

37. A method for the production of a sensor which comprises a medium and a hologram disposed therein, wherein an optical characteristic of the sensor varies as a result of a change of a property of the medium, the method comprising the steps of:
   forming a support medium by polymerising a mixture of polymerisable components and another component; disposing in the support medium a holographic recording material; and
   recording a holographic image; wherein the temperature at which the change of the physical property occurs is dependent on the amount of the another component present in the mixture.

38. The method according to claim 37, wherein the medium comprises a hydrogel.

39. The method according to claim 37, wherein the optical characteristic varies as a result of the medium undergoing a phase transition.

40. The method according to claim 39, wherein the component is a copolymer.

41. The method according to claim 37, wherein the component is N-isopropylacrylamide.

42. A method for the production of a silver-free holographic sensor, which comprises the steps of:
   forming a heterogeneous support medium having a hologram therein, by:
   (1) introducing throughout the volume of a first polymer a cross-linking monomer mixture;
   (2) reacting the monomer mixture to create a second polymer, which forms holographic polymer fringes, where the first and second polymer form the medium and wherein the extent of reaction is varied through the medium.

43. An array of discrete sensors, obtainable by a method for the production of a holographic sensor, which comprises the steps of:
   forming a heterogeneous support medium by introducing into a medium a component, reacting the component with the medium or a second component present in the medium, and varying the extent of reaction occurring in the medium;
   disposing in the support medium a holographic recording material; and recording a holographic image.

* * * * *

UNITED STATES PATENT AND TRADEMARK OFFICE
CERTIFICATE OF CORRECTION

PATENT NO. : 7,978,333 B2  Page 1 of 1
APPLICATION NO. : 11/572244
DATED : July 12, 2011
INVENTOR(S) : Christopher Robin Lowe, Anthony Peter James and Edward Rayne It is certified that error appears in the above-identified patent and that said Letters Patent is hereby corrected as shown below:

Column 9,
Line 22 (claim 23), "a hp of zones" should read --a plurality of zones--

Signed and Sealed this
Twenty-third Day of August, 2011

David J. Kappos
*Director of the United States Patent and Trademark Office*